United States Patent
Park et al.

(10) Patent No.: US 9,427,223 B2
(45) Date of Patent: Aug. 30, 2016

(54) FRAME DEVICE

(75) Inventors: Adrian Edward Park, Crownsville, MD (US); Charles Francis Knapp, Georgetown, KY (US)

(73) Assignee: Creative Surgical, LLC, Georgetown, KY (US)

( * ) Notice: Subject to any disclaimer, the term of this patent is extended or adjusted under 35 U.S.C. 154(b) by 660 days.

(21) Appl. No.: 12/595,154

(22) PCT Filed: Apr. 9, 2008

(86) PCT No.: PCT/US2008/059706
§ 371 (c)(1),
(2), (4) Date: May 26, 2010

(87) PCT Pub. No.: WO2008/124748
PCT Pub. Date: Oct. 16, 2008

(65) Prior Publication Data
US 2010/0249519 A1 Sep. 30, 2010

Related U.S. Application Data

(60) Provisional application No. 60/922,515, filed on Apr. 9, 2007.

(51) Int. Cl.
*A61B 1/32* (2006.01)
*A61B 17/02* (2006.01)

(52) U.S. Cl.
CPC .... *A61B 17/0218* (2013.01); *A61B 2017/0225* (2013.01)

(58) Field of Classification Search
USPC ........ 600/206, 208, 209; 606/108, 198, 199; 623/1.2, 1.12, 1.51; 267/1.5, 96, 97, 267/147, 167, 169
See application file for complete search history.

(56) References Cited

U.S. PATENT DOCUMENTS

| | | | |
|---|---|---|---|
| 4,994,032 A * | 2/1991 | Sugiyama et al. | 604/103.09 |
| 5,290,305 A * | 3/1994 | Inoue | 623/1.2 |
| 5,344,315 A | 9/1994 | Hanson | |
| 5,370,650 A * | 12/1994 | Tovey et al. | 606/151 |
| 5,702,419 A | 12/1997 | Berry | |
| 5,833,699 A * | 11/1998 | Chuter | 623/1.15 |
| 5,868,782 A * | 2/1999 | Frantzen | 623/1.15 |
| 6,200,336 B1 * | 3/2001 | Pavcnik et al. | 623/1.15 |
| 6,319,278 B1 | 11/2001 | Quinn | |
| 6,602,263 B1 * | 8/2003 | Swanson et al. | 606/153 |
| 6,705,986 B2 | 3/2004 | Fiegel | |
| 6,802,858 B2 | 10/2004 | Gambale | |
| 6,833,002 B2 * | 12/2004 | Stack et al. | 623/1.11 |
| 7,097,658 B2 * | 8/2006 | Oktay | 623/1.2 |
| 7,795,027 B2 * | 9/2010 | Hiles | 435/395 |
| 8,083,746 B2 * | 12/2011 | Novak | 606/88 |
| 2001/0004683 A1 | 6/2001 | Gambale | |
| 2003/0209835 A1 * | 11/2003 | Chun et al. | 264/339 |
| 2006/0135963 A1 | 6/2006 | Kick | |
| 2006/0253200 A1 * | 11/2006 | Bao et al. | 623/17.12 |

FOREIGN PATENT DOCUMENTS

WO WO 2005122953 A2 * 12/2005

* cited by examiner

*Primary Examiner* — Christian Sevilla
(74) *Attorney, Agent, or Firm* — Steptoe & Johnson LLP

(57) ABSTRACT

The devices and methods described can be used to create and maintain a working space within the lumen of an organ or between or among organs or tissue structures during medical procedures in order to elicit a diagnosis, biopsy, surgery, or therapy.

12 Claims, 10 Drawing Sheets

FRAME DEVICE

CLAIM OF PRIORITY

This application claims priority under 35 USC 371 to International Application No. PCT/US2008/059706 filed on Apr. 9, 2008, which claims priority to U.S. Provisional Application Ser. No. 60/922,515, filed Apr. 9, 2007, each of which is incorporated by reference in its entirety.

TECHNICAL FIELD

The invention relates to devices for use during surgical or non-surgical procedures in order to create work space.

BACKGROUND

Surgical procedures often require the expansion of the lumen of an organ in order to create and maintain a clear working space for performing a diagnosis, biopsy, surgery, therapy or the like. For example, the lumen of a segment of intestine may need to be expanded in order to perform surgery on a segment of the internal wall. This process can be technically demanding and even require an extra person to hold a conventional retractor or other instruments to meet the objective. Such a surgical procedure is even more challenging during minimally invasive surgery (MIS) where a trocar port is involved.

SUMMARY

The device and methods described here can significantly enhance the quality and economy of surgical or non-surgical procedures. The device and methods can be used to create and maintain a working space within the lumen of an organ, flexible object or group of objects during medical procedures in order to elicit a diagnosis, biopsy, surgery, or therapy such as resection, ligation, dissection and fulguration of the organ or object. The flexibility, and thinness of the device and the formation of a semi-rigid frame after deployment can make it suitable for surgery, especially minimally invasive surgery (MIS). The device can be pushed through a small tube or trocar when deployed and can be collapsed and pulled back into the tube when removed. In the deployed configuration, the device can expand to form, for example, a frame of cylindrical or spherical shape or of some other three dimensional shape. In another example, when deployed in the lumen of an organ, an expanded thin wired frame can push against the wall of the organ creating a working space through which surgical instruments can be introduced and manipulated. The device can be used, for example, to produce and maintain a working space in the lumen of the gastrointestinal tract, colon, or stomach and the like for procedures such as resection, ligation, dissection and fulguration. Surgical procedures such as resection, ligation, dissection and fulguration can be preformed on the wall of the organ through the enlarged space within the frame. The device is ideally suited for use in endolumenal surgery or therapy or translumenal surgery or therapy. The device can also be used for non-medical applications where the creation and maintenance of a working space is desired within the lumen of a flexible object or between flexible objects.

The endo frame device can eliminate the need for an extra person to hold tissue with a conventional retractor during surgery or MIS. A single operator can conduct the surgery and use and deploy the endo frame device. The operator can use and deploy the endo frame device using one hand only.

In addition, a single entry port can be used for a surgical procedure, simplifying the procedure, reducing cost and reducing risk of complications including infection.

In one aspect, an endo frame can include a flexible structure having a collapsed configuration and an expanded configuration, the expanded configuration being larger in diameter than the collapsed configuration. The collapsed configuration can have a diameter sufficient for insertion in a lumen through a trocar and the expanded configuration can have a rigidity sufficient to push against the wall of the lumen to create a working space. The collapsed configuration can be configured to be pushed through a sheath tube. The expanded configuration can have a cylindrical shape. The flexible structure can include circular rings at the ends of the cylindrical shape. The flexible structure can include longitudinal struts or an open woven mesh connecting the circular rings. The longitudinal struts can include spring steel. The circular rings can include woven wire springs with a hollow circumferential space. The circular rings can include a super elastic metal or a shape memory metal wire inside the hollow circumferential space. The flexible structure can have open ends and open sides.

In another aspect, a scroll endo frame can include a sheath, a sheet material, and a longitudinal strut including a roller system configured to roll or unroll the sheet material. The scroll endo frame can include a pusher tube, with a wire inside, configured to cause the roller system to roll or unroll the sheet material. The sheet material can be a coiled wire lattice sheet. The sheet material can include any suitable material such as spring steel or Nitinol. The longitudinal strut can connect to or disconnect from the pusher tube/wire through magnetic coupling.

In another aspect, a method of creating interluminal space of a patient can include introducing an endo frame into the lumen of the patient through a trocar; and expanding the endo frame inside the lumen. A single person can introduce and expand the endo frame. The person can introduce and expand the endo frame with one hand.

Additional objects, advantages and other novel features of the invention will be set forth in part in the description that follows and in part will become apparent to those skilled in the art upon examination of the foregoing or may be learned with the practice of the invention.

DETAILED DESCRIPTION

Figure 1A:
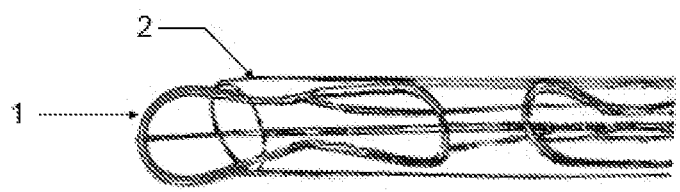
FIG. 1A is a side view of a cylindrical endo frame loaded in its flexible delivery sheath tubing.

The device and methods described here can be used to create and maintain a working space within the lumen of an organ or between or among organs or tissue structures during medical procedures in order to elicit a diagnosis, biopsy, surgery, or therapy. For example, the endo frame device can have a flexible structure capable of being deployed through a small diameter flexible tube and then expanding to a much larger diameter frame of cylindrical, spherical, or other shape. In another example, the endo frame device, when expanded, can form a hollow semi rigid structure of a cylindrical, spherical, conical, or other three dimensional shape. In the expanded configuration, the endo frame device can be capable of providing sufficient force to push against the wall of the organ thereby creating an interluminal space. The device can also be used to create and maintain a working space between or among flexible objects. The expanded endo frame can be open at each end and can have openings on the side to allow for surgical and diagnostic interventions. The endo frame can be collapsed and pulled back into the flexible tube for removal. The device can be used, for example, to produce and maintain a working space in the lumen of the gastrointestinal tract, colon, or stomach and the like for procedures such as resection, ligation, dissection and fulguration. The flexibility and size of the collapsed endo frame can allow it to be pushed and removed through a trocar during minimally invasive surgery. The device can also be used for endolumenal surgery or therapy or translumenal surgery or therapy as well as for non-surgical applications. The flexibility, and thinness of the device and the formation of a rigid frame after deployment make the device suitable for expanding luminal spaces during medical procedures, especially during minimally invasive surgery.

The endo frame can include a flexible structure having a collapsed configuration and an expanded configuration, the expanded configuration being larger in diameter than the collapsed configuration. The collapsed configuration can have a diameter sufficient for insertion in a lumen through a trocar and the expanded configuration can have a rigidity sufficient to push against the wall of the lumen to create a working space. The collapsed configuration can be configured to be pushed through a sheath tube. The expanded configuration can have a cylindrical shape. The flexible structure can include circular rings at the ends of the cylindrical shape. The flexible structure can include longitudinal struts or an open woven mesh connecting the circular rings. The longitudinal struts can include spring steel. The number of longitudinal struts around the circumference of the end rings can vary and depend upon the application. The circular rings can include woven wire springs with a hollow circumferential space. The circular rings can include a super elastic metal or a shape memory metal wire inside the hollow circumferential space. The flexible structure can have open ends and open sides.

For example, the primary components of a cylindrically shaped endo frame can include two circular rings which can include coiled wire such as spring coil rings. A continuous length of super elastic wire such as Nitinol can pass through the spring coil rings. The super elastic wire can help to ensure that the end rings will not crimp when loaded into the applier. In addition, Nitinol wire in the shape memory mode can also enhance strength when in contact with body heat. The two circular rings can be connected with semi rigid longitudinal wire struts to form the cylindrical shape of the endo frame and to ensure tissue support when deployed.

In another example, the device can expand to form a frame of spherical shape. For a spherical shape, numerous circular rings can be connected to each other to form the desired shape upon deployment. Other shapes can include conical, hour glass, or other three dimensional shapes.

During a surgical procedure, an endo frame device can be introduced in the lumen of a patient through a trocar. The endo frame device can be collapsed and pushed through a small tube or trocar. After deployment inside the lumen of an organ, an expanded thin wired endo frame can push against the wall of the organ creating a working space through which surgical instruments can be introduced and manipulated. At the end of the surgical procedure, the endo frame is collapsed and pulled back into the tube or trocar for removal.

The endo frame device can eliminate the need for an extra person to hold tissue with a conventional retractor during surgery or MIS. A single operator can conduct the surgery and use and deploy the endo frame device. The operator can use and deploy the endo frame device using one hand only. In addition, a single entry port can be used for a surgical procedure, simplifying the procedure, reducing cost and reducing risk of complications including infection.

Figure 1B:
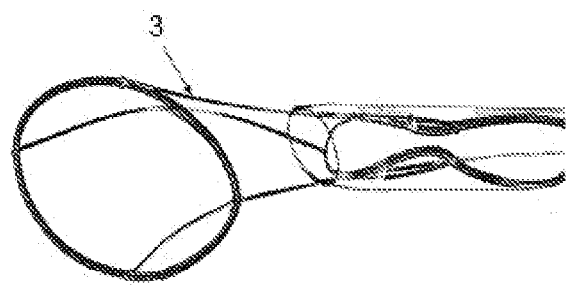
FIG. 1B is a side view of a cylindrical endo frame partially deployed from its sheath.
Figure 1C:
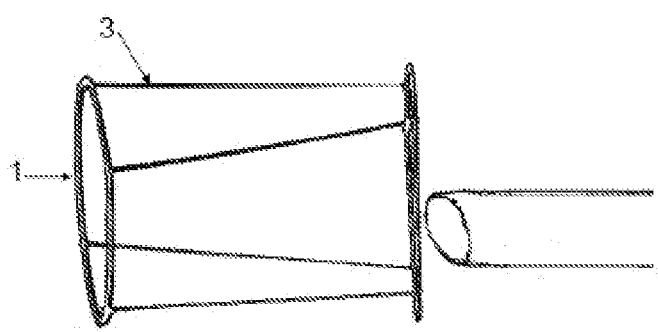
FIG. 1C is a side view of a fully deployed cylindrical endo frame.

Referring to FIGS. 1A-B, the main components of a cylindrically shaped endo frame can include two circular rings 1 made of coiled wire such as spring coil rings with a continuous length of super elastic wire such as Nitinol passing through the spring coil rings. The super elastic wire can help to ensure that the circular rings will not crimp when loaded into the applier. Nitinol wire in the shape memory mode can also enhance strength when in contact with body heat. The two circular rings can be connected with semi rigid longitudinal wire struts 3 to form the cylindrical shape of the structure and ensure tissue support when the endo frame is deployed. The device can be pushed through a small tube or trocar 2, deployed, and then collapsed and pulled back into the tube when removed. In the deployed configuration, the device expands to form a frame of cylindrical or spherical shape for example. For an endo frame of a spherical shape, numerous circular rings can connected to each other to form the desired shape upon deployment. The expanded thin wired endo frame when deployed in the lumen of an organ pushes against the wall of the organ creating a working space through which surgical instruments can be introduced and manipulated.

The device can be loaded in a flexible sheath 2 and pushed through a small tube or trocar when deployed. It can be collapsed and pulled back into the sheath tube 2 and removed by a hooked guide wire or similar instrument. In the deployed configuration, the device can expand to form a frame of cylindrical or spherical shape. When deployed in the lumen of an organ, the expanded thin wired endo frame pushes against the wall of the organ creating a working space through which surgical instruments can be introduced and manipulated.

Figure 2A:
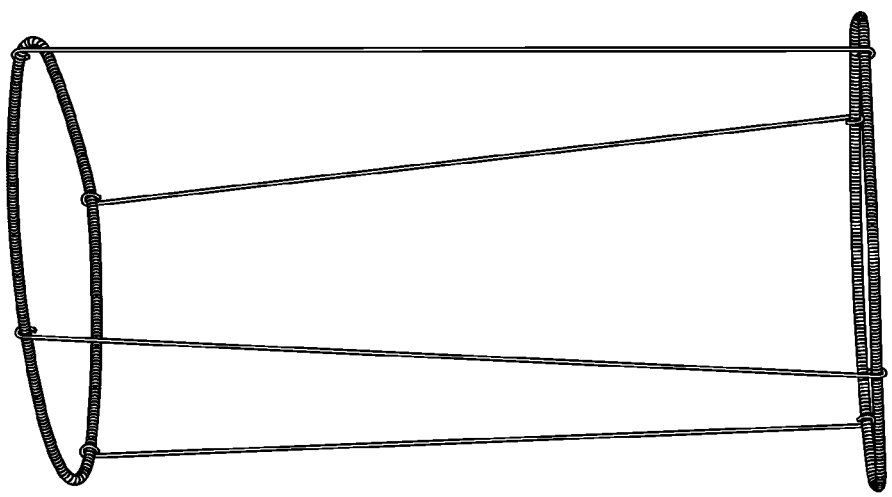
FIG. 2A shows a fully deployed cylindrical endo frame.
Figure 2B:
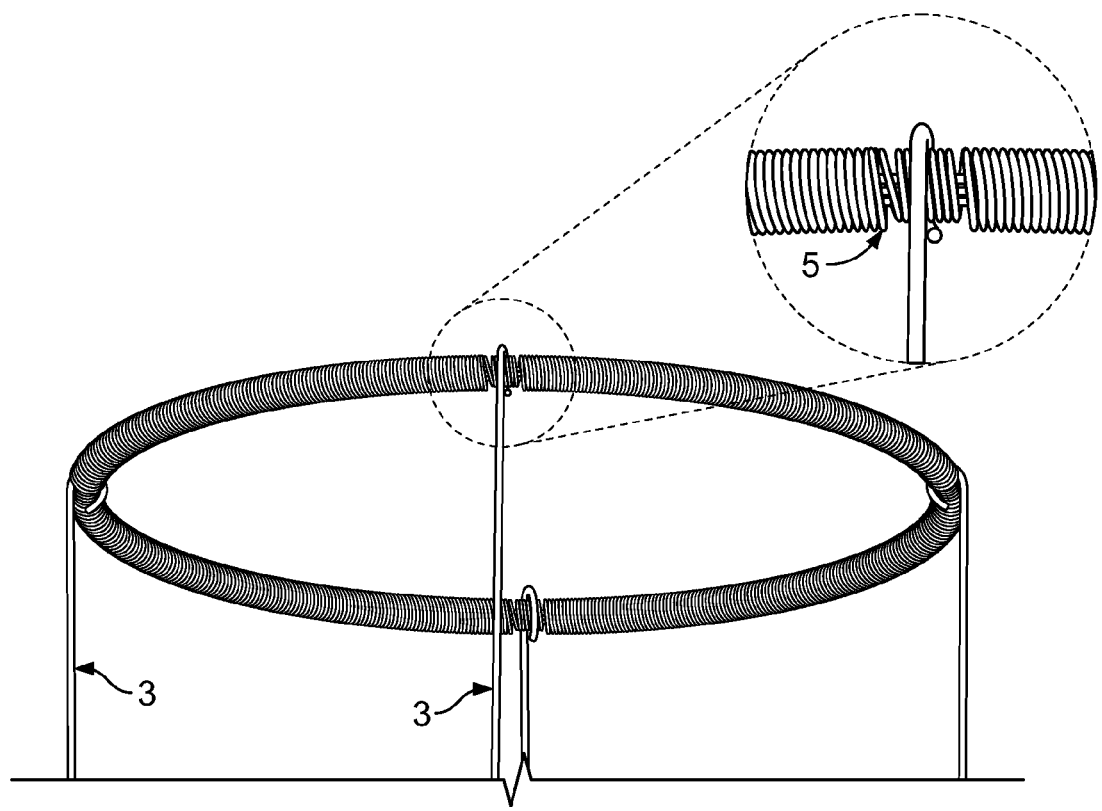
FIG. 2B shows a close up view of a circular ring and semi rigid longitudinal wire struts of a cylindrical endo frame and a close up view of a circular ring made of coiled wire with a continuous length of super elastic wire inside the ring and a semi rigid longitudinal wire strut attached to the ring.

Referring to FIGS. 2A-B a cylindrically shaped endo frame can include two circular rings made of coiled wire such as spring coil rings with a continuous length of super elastic wire 5 such as Nitinol passing through the spring coil ring. The super elastic wire can help to ensure that the end rings will not crimp when loaded into the applier. In addition, Nitinol wire in the shape memory mode can enhance the strength and help maintain shape when in contact with body heat. Semi rigid longitudinal wire struts 3 can be connected to the two circular end rings to form the cylindrical shape of the structure and tissue support when deployed.

Figure 3A:
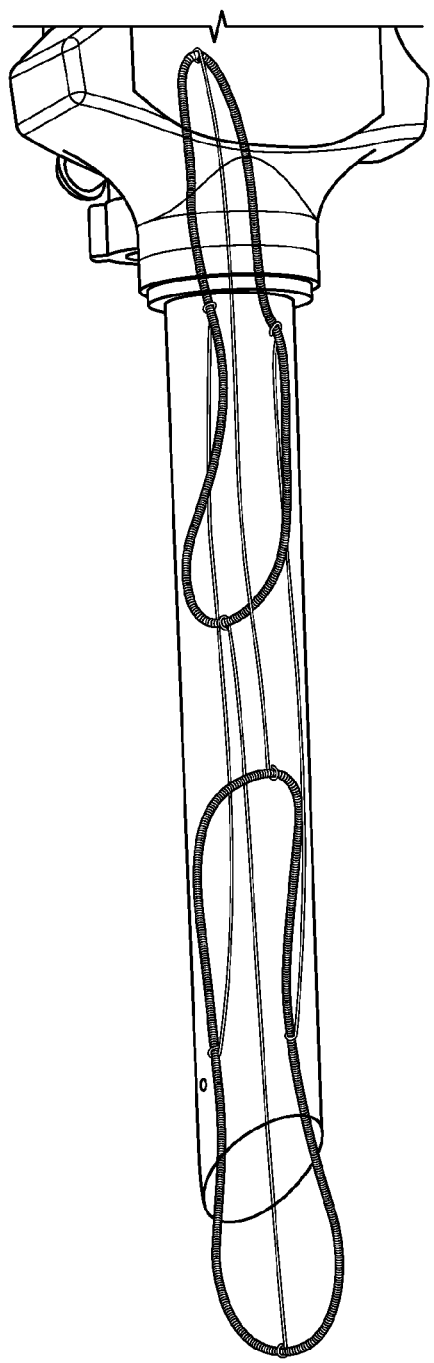
FIG. 3A shows a cylindrical endo frame loaded in applier.
Figure 3B:
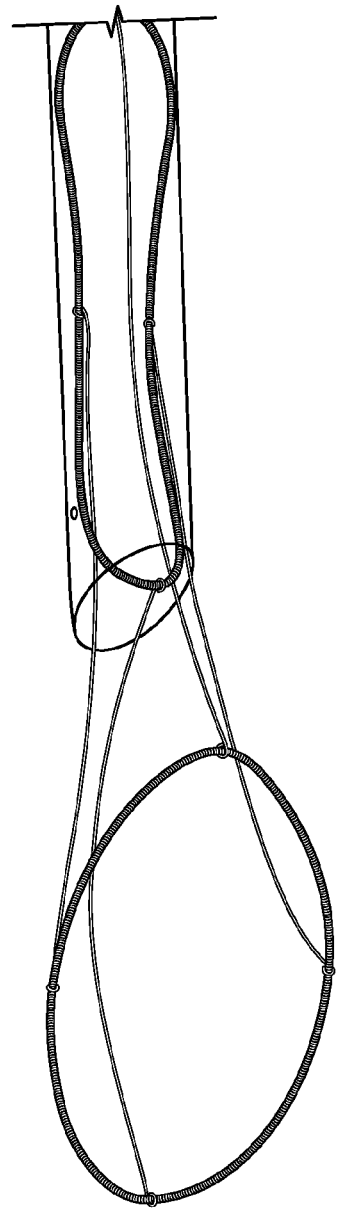
FIG. 3B shows a cylindrical endo frame being pushed out of an applier.
Figure 3C:
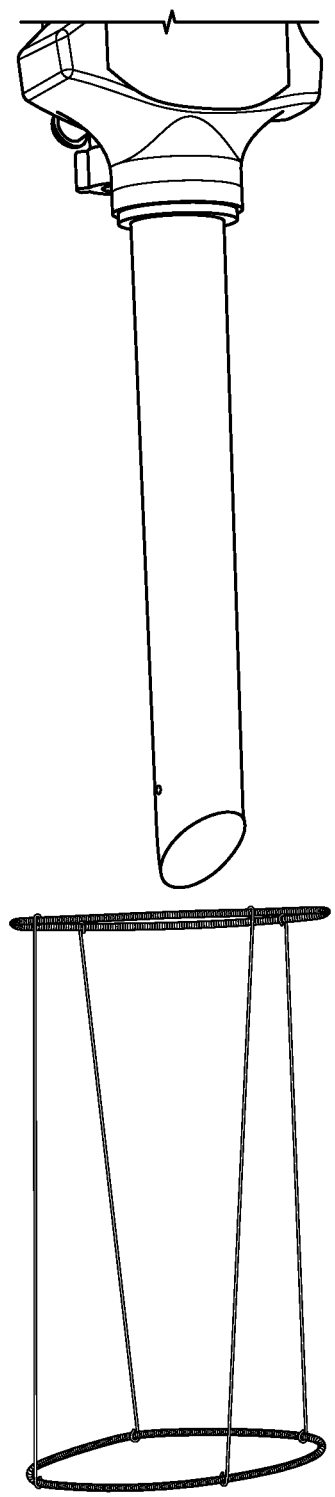
FIG. 3C shows a fully deployed cylindrical endo frame.

Referring to FIGS. 3A-C, an endo frame can be loaded in an applier, pushed out of the applier, and fully deployed into a cylindrical endo frame.

Another possible design of the endo frame, can be a scroll endo frame which can include a sheath, a sheet material, and a longitudinal strut including a roller system configured to roll or unroll the sheet material. The scroll endo frame can include a pusher tube, with a wire inside, configured to cause the roller system to roll or unroll the sheet material. The sheet material can be a coiled wire lattice sheet and can include a spring metal such as spring steel or Nitinol. The longitudinal strut can connect to or disconnect from the pusher tube/wire through magnetic coupling.

For example, a cylindrically shaped scroll endo frame can include a coiled, thin wire, lattice sheet which, when unrolled, forms a cylindrical wire frame which can push against the wall of the lumen thereby creating a working space. The lattice sheet can be held in its coiled position through the use of a sheath. The coiled lattice frame can be pushed out of the sheath by a small diameter pusher tube. The pusher tube can have a wire inside that, when twisted, causes a small roller system inside a longitudinal main strut to unroll the lattice frame. The circular shape of a semi rigid scroll endo frame can be maintained by the stored energy in the springy lattice sheet. The other end of the lattice sheet can be permanently attached to the longitudinal main strut. The roller system in the main longitudinal strut of the lattice sheet can be connected to the flexible pusher tube/twist wire by a magnetic coupling/lock arrangement.

During a surgical procedure, a scroll endo frame device can be introduced in the lumen of a patient through a trocar. The scroll endo frame device can be held in its coiled configuration inside a sheath tube. The scroll endo frame can be pushed out of the sheath tube using a pusher tube and deployed inside the lumen of an organ. The scroll endo frame can include a sheet material connected to a longitudinal strut. A wire inside the pusher tube can cause a roller system inside the longitudinal strut to unroll the sheet material. The pusher tube can be disconnected from and reconnected to the longitudinal strut through magnetic coupling. The deployed scroll endo frame can push against the wall of the organ creating a working space through which surgical instruments can be introduced and manipulated. At the end of the surgical procedure, the pusher tube can be reconnected to the longitudinal strut and the wire inside the pusher tube can be twisted to roll the sheet material back to its coiled configuration. The scroll endo frame can be then pulled back into the tube or trocar for removal.

The scroll endo frame device also can eliminate the need for an extra person to hold tissue with a conventional retractor during surgery or MIS. A single operator can conduct the surgery and use and deploy the scroll endo frame device. The operator can use and deploy the endo frame device using one hand only. In addition, a single entry port can be used for a surgical procedure, simplifying the procedure, reducing cost and reducing risk of complications including infection.

Figure 4A:
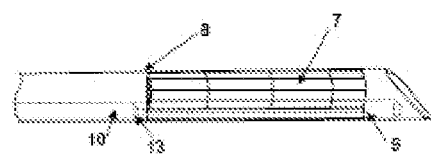
FIG. 4A is a side view of a scroll endo frame in a rolled up position and housed in its deployment sheath.
Figure 4B:
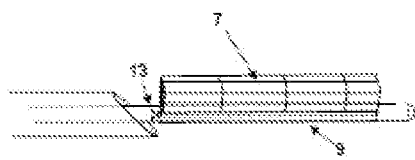
FIG. 4B is a side view of a scroll endo frame in a rolled up position and pushed from its deployment sheath.
Figure 4C:
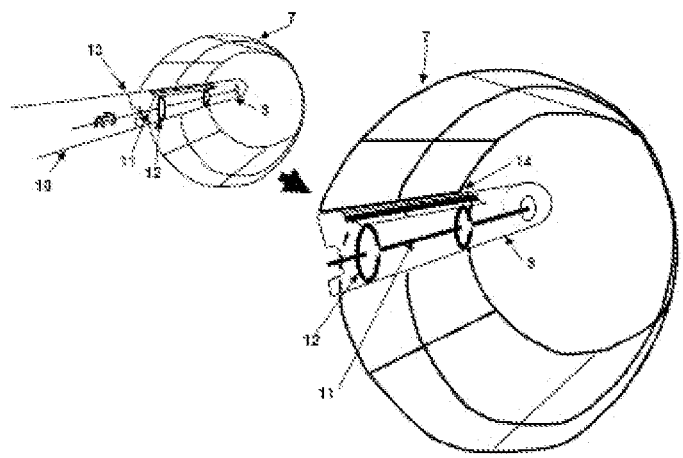
FIG. 4C is an end view of a fully deployed scroll endo frame and a close up view showing a main strut, a roller mechanism and a pusher tube/twist wire arrangement.
Figure 5A:
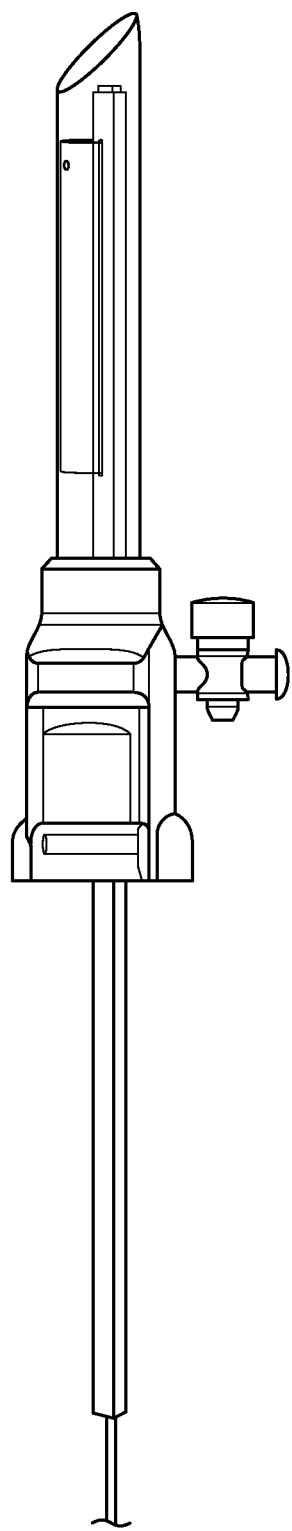
FIGS. 5 A-D show a sequence of images of an endo frame loaded in a trocar, being pushed out of a trocar, completely out of a trocar, and full deployed.
Figure 5B:
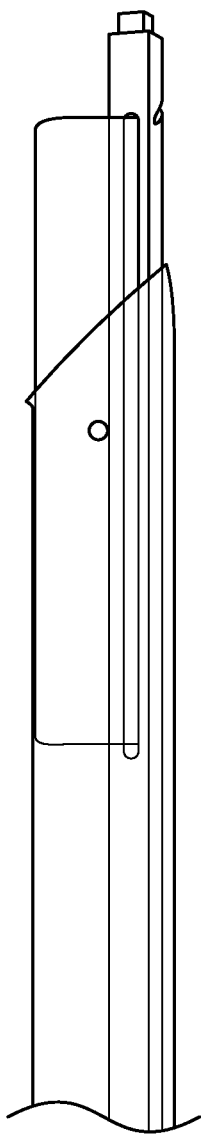
Figure 5C:
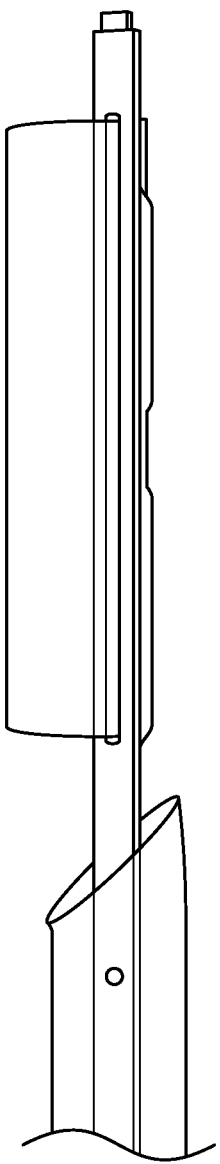
Figure 5D:
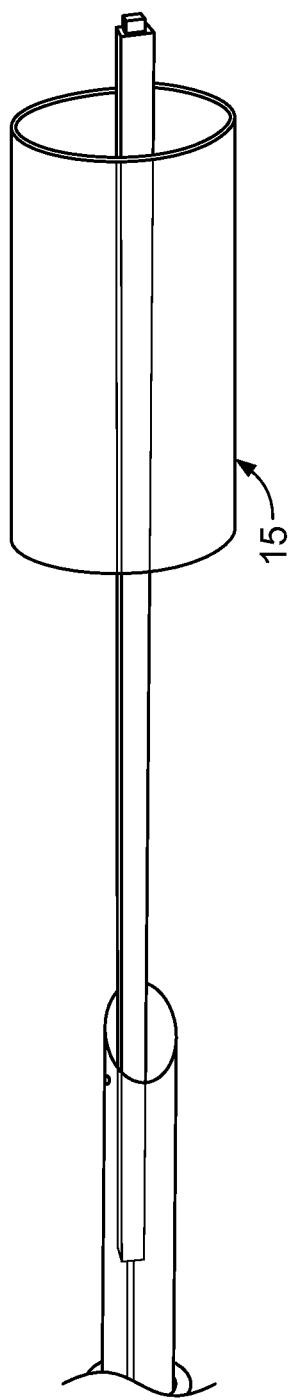

Referring to FIGS. 4A-C, a scroll endo frame using a coiled, thin wire, lattice sheet 7 which, when unrolled, forms a cylindrical wire frame which functions as described above. The lattice sheet is held in its coiled position through the use of a thin walled sheath 8. The coiled lattice frame can be pushed out of the sheath by a small diameter pusher tube 10. The pusher tube can have a wire 11 inside that, when twisted, causes a small roller system 12 inside a longitudinal main strut 9 to unroll the lattice frame. The circular shape of the semi rigid scroll endo frame can be maintained by the stored energy in the springy lattice material which can be made from Nitinol or a spring metal. The other end 14 of the lattice sheet can be permanently attached to the longitudinal main strut 9. The roller system 12 in the main longitudinal strut of the lattice sheet 7 can be connected to the flexible pusher tube/twist wire by a magnetic coupling/lock arrangement 13.

The pusher tube/twist wire arrangement can be held to the main longitudinal strut of the scroll endo frame by a magnetic coupling. The pusher tube/twist wire can be separated from the main strut by a push of the twist wire to complete the deployment of the scroll endo frame. Reattachment of the pusher tube/twist wire to the main longitudinal strut can be aided by magnetic attraction during roll up and removal of the scroll endo frame.

Referring to FIGS. 5 A-D, a scroll endo frame can be loaded in a trocar, pushed out of a trocar, and fully unrolled. The sheet material 15 can be made of spring steel or Nitinol. When fully unrolled, the scroll endo frame can push against the wall of a lumen thereby creating a working space through which surgical instruments can be introduced and manipulated.

Figure 6A:
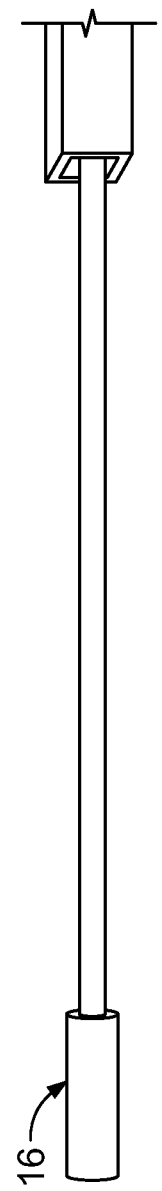
FIGS. 6 A-C show a scroll endo frame knob shaft to roll and unroll the frame.
Figure 6B:
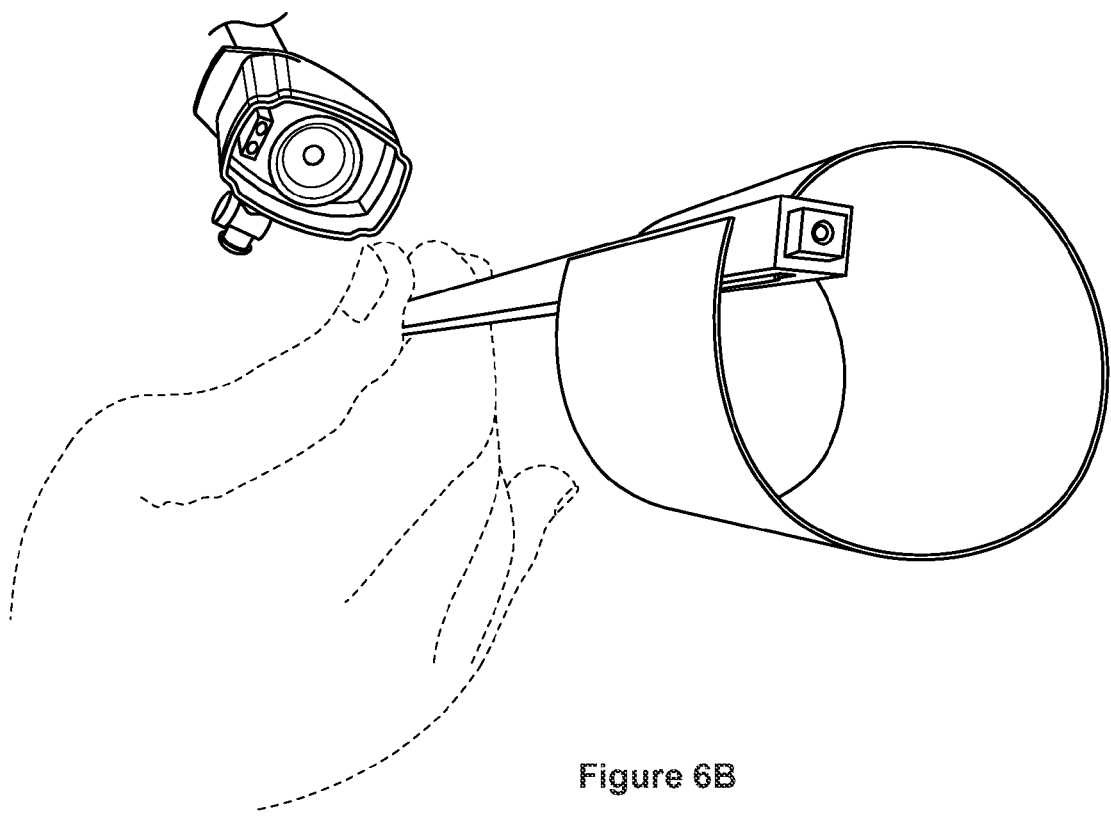
Figure 6C:
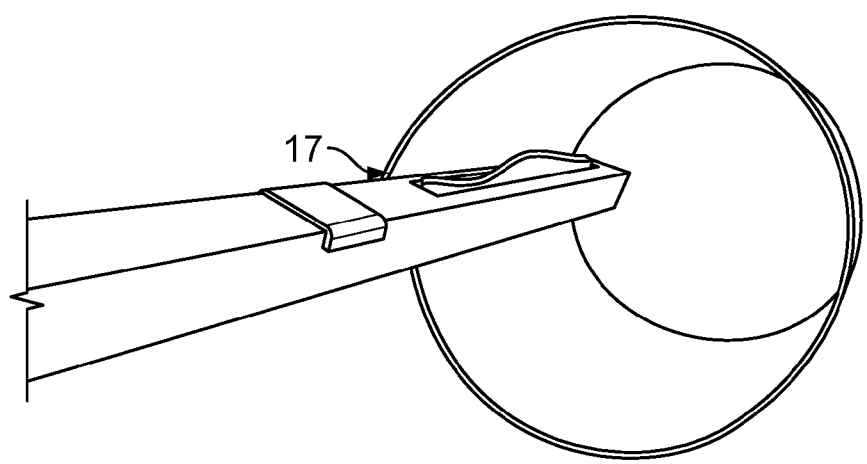

Referring to FIGS. 6 A-C a scroll endo frame can include a knob shaft 16 inside a pusher tube to roll and unroll the sheet material. The longitudinal strut 17 can include a disconnect/reconnect point separating the longitudinal strut from the pusher tube.

Figure 7:
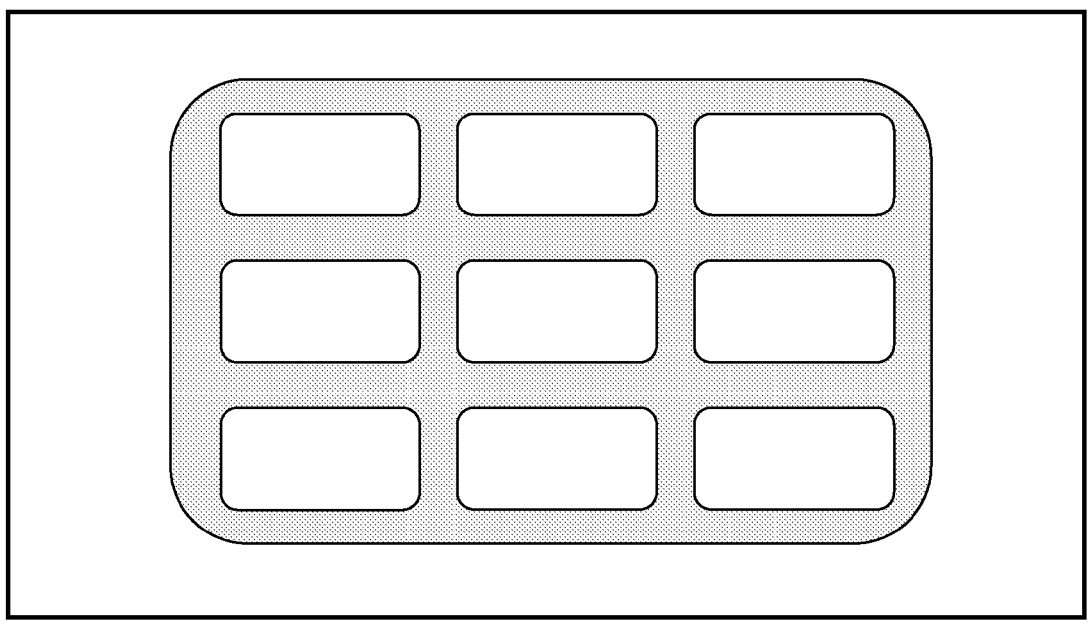
FIG. 7 shows a scroll endo frame sheet pattern.

A lattice sheet of a scroll endo frame can have the pattern of FIG. 7. The lattice sheet can include any suitable material such as spring steel or Nitinol.

For surgical applications, the entire endo frame device can be made of materials that can be sterilized. In addition, the entire assembly is capable of being prepackaged, sterile, in a suitable container.

Other embodiments are within the scope of the following claims.

What is claimed is:

1. An endo frame comprising a flexible structure comprising an open woven mesh or longitudinal struts connecting circular rings and having a collapsed configuration and an expanded configuration, the expanded configuration being larger in diameter than the collapsed configuration and in the expanded configuration the circular rings are substantially perpendicular to a longitudinal axis of the endo frame and has a cylindrical shape, wherein the collapsed configuration has a diameter sufficient for insertion into a lumen through a tube or trocar prior to converting to the expanded configuration and the expanded configuration converts to the collapsed configuration for removal from the lumen through a tube or trocar, wherein in the collapsed configuration the circular rings are substantially parallel to the longitudinal axis of the endo frame and at least one end ring is in an oval shape having a long axis oriented substantially in the direction of the longitudinal axis of the endo frame, and wherein the endo frame creates and maintains a working space in a body during medical procedures.

2. The endo frame of claim 1, wherein the collapsed configuration has a diameter sufficient for insertion in a lumen through a trocar and the expanded configuration has a rigidity sufficient to push against the wall of the lumen to create a working space.

3. The endo frame of claim 1, wherein the longitudinal struts include spring steel.

4. The endo frame of claim 1, wherein the circular rings include woven wire springs with a hollow circumferential space.

5. The endo frame of claim 4, wherein the circular rings include a super elastic metal wire inside the hollow circumferential space.

6. The endo frame of claim 4, wherein the circular rings include a shape memory metal wire inside the hollow circumferential space.

7. The endo frame of claim 1, wherein the flexible structure has open ends and open sides.

8. The endo frame of claim 1, wherein the collapsed configuration is configured to be pushed through a sheath tube.

9. A method of creating interluminal space of a patient comprising:
    introducing the endo frame of claim 1 into the lumen of the patient through a trocar; and
    expanding the endo frame inside the lumen.

10. The method of claim 9, wherein a single person introduces and expands the endo frame.

11. The method of claim 10, wherein the person introduces and expands the endo frame with one hand.

12. The endo frame of claim 1, wherein in the expanded configuration each longitudinal strut has proximal and distal ends which are in alignment with those of the other longitudinal struts, and in the collapsed configuration proximal and distal ends of at least one longitudinal strut are axially offset from the other struts.

* * * * *